United States Patent
Tylutki et al.

(10) Patent No.: US 9,846,110 B2
(45) Date of Patent: Dec. 19, 2017

(54) PARTICULATE MATTER SENSOR DIAGNOSTIC SYSTEM AND METHOD

(71) Applicant: GM Global Technology Operations LLC, Detroit, MI (US)

(72) Inventors: Vincent J. Tylutki, Livonia, MI (US); Igor Anilovich, Walled Lake, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 273 days.

(21) Appl. No.: 14/728,238

(22) Filed: Jun. 2, 2015

(65) Prior Publication Data
US 2016/0356693 A1    Dec. 8, 2016

(51) Int. Cl.
| | |
|---|---|
| *G01N 7/00* | (2006.01) |
| *G01N 15/06* | (2006.01) |
| *F01N 11/00* | (2006.01) |
| *G01M 15/10* | (2006.01) |
| *G01N 15/00* | (2006.01) |
| *F01N 3/021* | (2006.01) |

(52) U.S. Cl.
CPC ......... *G01N 15/0656* (2013.01); *F01N 11/00* (2013.01); *F01N 11/002* (2013.01); *G01M 15/102* (2013.01); *F01N 3/021* (2013.01); *F01N 2550/00* (2013.01); *F01N 2560/05* (2013.01); *F01N 2900/0602* (2013.01); *G01N 2015/0046* (2013.01); *Y02T 10/47* (2013.01)

(58) Field of Classification Search
CPC ....... G01N 15/0656; G01N 2015/0046; G01N 15/06; G01N 1/205; G01N 2001/2223; G01N 1/2202; G01M 15/102; G01M 15/104; F01N 11/00; F01N 11/002; F01N 2900/0602; F01N 3/021; F01N 2550/00; F01N 2560/05; F01N 11/007; F01N 2550/02; F02D 41/1495; F02D 41/1441; F02B 3/06
USPC ..... 73/23.33, 28.01, 114.69, 114.71; 60/277, 60/276
See application file for complete search history.

(56) References Cited

U.S. PATENT DOCUMENTS

| | | | | |
|---|---|---|---|---|
| 5,251,564 | A | * 10/1993 | Rim ......................... | F01N 3/02 110/216 |
| 5,445,128 | A | * 8/1995 | Letang ................. | B60K 31/045 123/436 |
| 5,636,331 | A | * 6/1997 | Klinefelter ........... | G06K 15/028 347/193 |

(Continued)

*Primary Examiner* — John Fitzgerald
*Assistant Examiner* — Truong D Phan

(57) ABSTRACT

A diagnostic module for diagnosing a particulate matter sensor in a vehicle includes a sensor mode selection module, a heater power detector, and a protection tube diagnostic module. The sensor mode selection module selects a regeneration mode for the particulate matter sensor from among a plurality of operation modes. The regeneration mode regenerates the particulate matter sensor. The heater power detector determines a voltage output based on a voltage applied to the particulate matter sensor. The voltage output corresponds to operation of the particulate matter sensor in the selected mode. The protection tube diagnostic module performs a diagnostic of the particulate matter sensor. The protection tube diagnostic module selectively diagnoses a fault in the particulate matter sensor based on the voltage output determined during the regeneration mode and a regeneration power threshold.

14 Claims, 6 Drawing Sheets

(56) References Cited

U.S. PATENT DOCUMENTS

| | | | |
|---|---|---|---|
| 2004/0161596 A1* | 8/2004 | Taoka | B01D 46/2429 428/304.4 |
| 2007/0046292 A1* | 3/2007 | Plett | G01R 31/3624 324/429 |
| 2007/0125349 A1* | 6/2007 | Zanini-Fisher | F01N 11/00 123/679 |
| 2009/0094963 A1* | 4/2009 | Mizoguchi | F01N 3/101 60/286 |
| 2011/0209460 A1* | 9/2011 | He | F01N 9/002 60/274 |
| 2011/0252768 A1* | 10/2011 | Baumann | F01N 11/00 60/274 |
| 2012/0031077 A1* | 2/2012 | Aoki | F01N 13/008 60/276 |
| 2012/0260636 A1* | 10/2012 | Hashida | F01N 11/00 60/276 |
| 2013/0031892 A1* | 2/2013 | Nagaoka | F01N 3/0842 60/274 |
| 2013/0298535 A1* | 11/2013 | Aoki | F02D 41/1466 60/276 |
| 2013/0298537 A1* | 11/2013 | Aoki | F01N 3/023 60/311 |
| 2015/0244313 A1* | 8/2015 | McNamara | H01L 31/02021 136/244 |

* cited by examiner

PARTICULATE MATTER SENSOR DIAGNOSTIC SYSTEM AND METHOD

FIELD

The present disclosure relates to a fault diagnostic method and system for a particulate matter sensor in a vehicle.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Diesel engine operation involves combustion that generates exhaust gas. During combustion, an air/fuel mixture is delivered through an intake valve to cylinders and is combusted therein. After combustion, the piston forces the exhaust in the cylinders into an exhaust system. The exhaust may contain emissions such as oxides of nitrogen (NOx) and carbon monoxide (CO).

An exhaust treatment system is typically used to reduce vehicle emissions. A diesel particulate filter can be used in the exhaust system for diesel engines. The diesel particulate filter removes particulate matter from the exhaust. The particulate matter is often referred to as soot. A diesel-powered vehicle equipped with a functioning filter will emit no visible smoke from its exhaust pipe.

The exhaust treatment system may also include a particulate matter sensor. The particulate matter sensor detects particulate matter flowing in the exhaust. Based on a signal from the PM sensor, a control module can monitor the performance of a particulate filter and determine the amount of particulate matter being released into the atmosphere.

SUMMARY

In a feature, a diagnostic module for diagnosing a particulate matter sensor in a vehicle is disclosed. The diagnostic module includes: a sensor mode selection module, a heater power detector, and a protection tube diagnostic module. The sensor mode selection module selects a regeneration mode for the particulate matter sensor from among a plurality of operation modes. The regeneration mode regenerates the particulate matter sensor. The heater power detector determines a voltage output based on a voltage applied to the particulate matter sensor. The voltage output corresponds to operation of the particulate matter sensor in the selected mode. The protection tube diagnostic module performs a diagnostic of the particulate matter sensor. The protection tube diagnostic module selectively diagnoses a fault in the particulate matter sensor based on the voltage output determined during the regeneration mode and a regeneration power threshold.

In further features, the protection tube diagnostic module diagnoses the fault in the particulate matter sensor in response to the voltage output determined during the regeneration mode being less than the regeneration power threshold.

In further features, the diagnostic module further includes a flow rate determination module that determines a flow rate characteristic of exhaust flowing through an exhaust treatment system of the vehicle. The protection tube diagnostic module performs the diagnostic when the flow rate characteristic is greater than or equal to a minimum flow rate threshold.

In further features, the plurality of operation modes includes a protective heating mode. The heater power detector determines the voltage output as a protective voltage output in response to the selected mode being the protective heating mode and the voltage output as a regeneration voltage output in response to the selected mode being the regeneration mode. The protection tube diagnostic module diagnoses the fault in the particulate matter sensor in response to the protective voltage output being less than a protective power threshold and the regeneration voltage output being less than the regeneration power threshold. The protection tube diagnostic module diagnoses the particulate matter sensor as normal in response to either the protective voltage output being greater than the protective power threshold or the regeneration voltage output being greater than the regeneration power threshold.

In further features, the heater power detector includes a voltage sensor.

In further features, the protection tube diagnostic module stores a diagnostic trouble code in response to diagnosing the fault in the particulate matter sensor.

In further features, an exhaust treatment system of a vehicle includes: the diagnostic module, a particulate matter sensor, a temperature mode module, and a heater power module. The particulate matter sensor detects particulate matter in exhaust and includes a heating element. The temperature mode module controls a temperature of the particulate matter sensor to a desired temperature. The heater power module applies a voltage to the heating element based on the desired temperature.

In further features of the exhaust treatment system, the temperature module controls the temperature of the particulate matter sensor to a combustion temperature in the regeneration mode.

In further features of the exhaust treatment system, the plurality of operation modes includes a protective heating mode. The temperature module controls the temperature of the particulate matter sensor to a value greater than or equal to a dew point in the protective heating mode and controls the temperature of the particulate matter sensor to a combustion temperature in the regeneration mode. The heater power detector determines the voltage output as a protective voltage output in response to the selected mode being the protective heating mode and the voltage output as a regeneration voltage output in response to the selected mode being the regeneration mode. The protection tube diagnostic module diagnoses the fault in the particulate matter sensor in response to the protective voltage output being less than a protective power threshold and the regeneration voltage output being less than the regeneration power threshold. The protection tube diagnostic module diagnoses the particulate matter sensor as normal in response to either the protective voltage output being greater than the protective power threshold or the regeneration voltage output being greater than the regeneration power threshold.

In a feature, a diagnostic method for diagnosing a particulate matter sensor in a vehicle is disclosed. The diagnostic method includes: selecting a regeneration mode for the particulate matter sensor from among a plurality of operation modes, wherein the regeneration mode regenerates the particulate matter sensor; determining a voltage output based on a voltage applied to the particulate matter sensor, where the voltage output corresponds to operation of the particulate matter sensor in the selected mode; and selectively diagnosing a fault in the particulate matter sensor based on the voltage output determined during the regeneration mode and a regeneration power threshold.

In further features, the diagnostic method further includes diagnosing the fault in the particulate matter sensor in response to the voltage output determined during the regeneration mode being less than the regeneration power threshold.

In further features, the diagnostic method further includes: determining a flow rate characteristic of exhaust flowing through an exhaust treatment system of the vehicle; and the selectively diagnosing the fault in the particulate matter sensor is performed when the flow rate characteristic is greater than or equal to a minimum flow rate threshold.

In further features, the diagnostic method further includes: selecting a protective heating mode for the particulate matter sensor from among the plurality of operation modes; determining the voltage output as a protective voltage output in response to the selected mode being a protective heating mode and the voltage output as a regeneration voltage output in response to the selected mode being the regeneration mode; diagnosing the fault in the particulate matter sensor in response to the protective voltage output being less than a protective power threshold and the regeneration voltage output being less than the regeneration power threshold; and diagnosing the particulate matter sensor as normal in response to either the protective voltage output being greater than the protective power threshold or the regeneration voltage output being greater than the regeneration power threshold.

In further features the voltage output is determined using a voltage sensor.

In further features, the diagnostic method further includes storing a diagnostic trouble code in response to diagnosing the fault in the particulate matter sensor.

In further features, the diagnostic method further includes: using a heating element disposed in the particulate matter sensor, controlling a temperature of the particulate matter sensor to a desired temperature; and applying a voltage to the heating element based on the desired temperature.

In further features, the temperature of the particulate matter sensor is controlled to a combustion temperature in the regeneration mode.

In further features, the diagnostic method further includes: selecting a protective heating mode for the particulate matter sensor from among the plurality of operation modes; determining the voltage output as a protective voltage output in response to the selected mode being a protective heating mode and the voltage output as a regeneration voltage output in response to the selected mode being the regeneration mode; diagnosing the fault in the particulate matter sensor in response to the protective voltage output being less than a protective power threshold and the regeneration voltage output being less than the regeneration power threshold; and diagnosing the particulate matter sensor as normal in response to either the protective voltage output being greater than the protective power threshold or the regeneration voltage output being greater than the regeneration power threshold. The temperature of the particulate matter sensor is controlled to a combustion temperature in the regeneration mode, and the temperature of the particulate matter sensor is controlled to a value greater than or equal to a dew point in the protective heating mode.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

An exhaust treatment system may include a particulate matter (PM) sensor for detecting particulate matter in exhaust gas flowing through the exhaust treatment system. In the event the PM sensor is plugged, or alternatively located outside of the exhaust treatment system, the PM sensor may not receive exhaust. Accordingly, a control module may not be able to monitor the performance of a particulate filter and/or determine the amount of particulate matter being released into the atmosphere.

Diagnostic systems and methods according to the principal of the present disclosure determine whether exhaust is flowing through a PM sensor. The temperature of the PM sensor is controlled according to two operation modes: a protective heating mode and a regeneration mode. For example, a power module may apply a drive signal to the PM sensor to control the temperature of the PM sensor. Based on the electrical power needed to maintain the temperature of the PM sensor for the operation modes, the PM sensor may be diagnosed as having a fault or operating properly.

Figure 1:
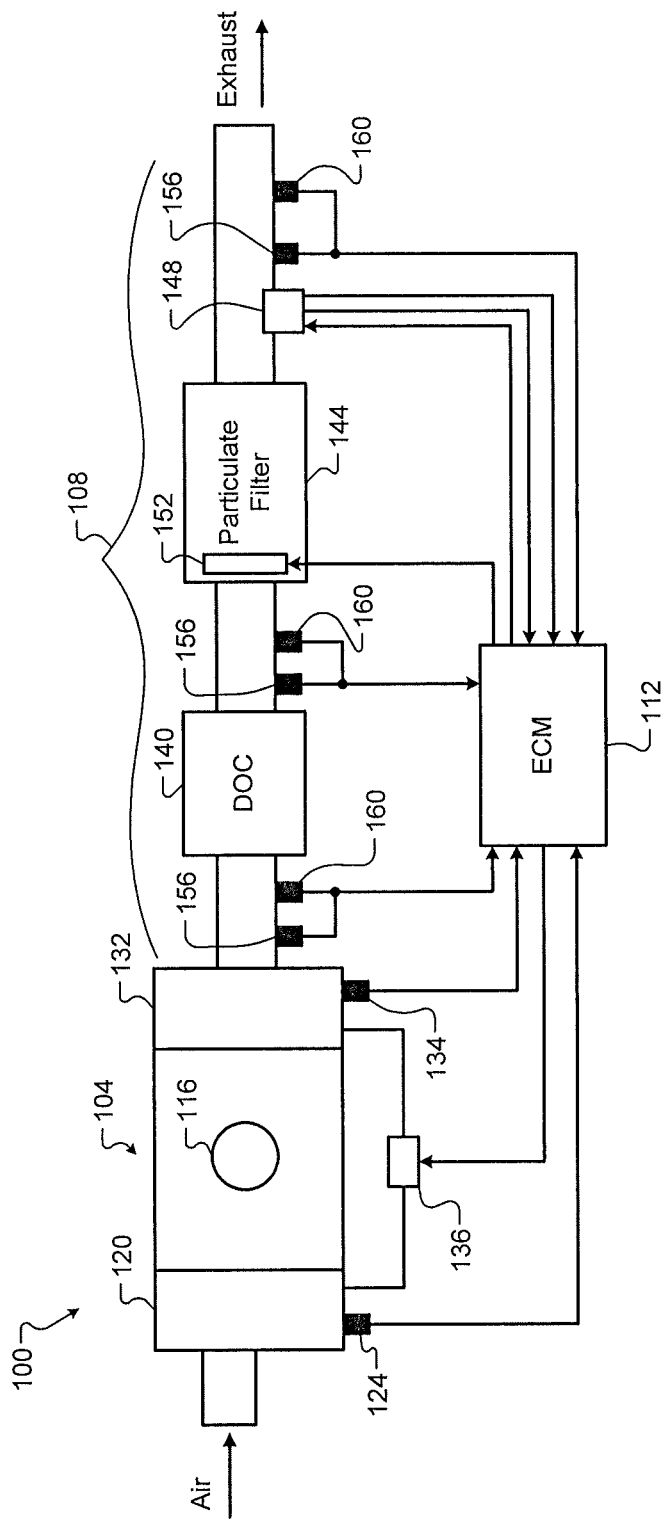
FIG. 1 is an functional block diagram of an example engine system according to the principles of the present disclosure.

Referring now to FIG. 1, an example diesel engine system 100 is illustrated in accordance with the present disclosure. The diesel engine system 100 is merely exemplary in nature. The PM sensor diagnostic technique described herein may be implemented in various engine systems that include a particulate filter. The engine systems may include gasoline direct injection engine systems and homogeneous charge compression ignition engine systems. For ease of the discussion, the disclosure will be discussed in the context of a diesel engine system.

The engine system 100 includes a diesel engine 104 and an exhaust treatment system 108. An engine control module (ECM) 112 regulates operation of the engine system 104 and the exhaust treatment system 108. The engine 104 may include a cylinder 116, an intake manifold 120, and a mass air flow (MAF) sensor 124. Air flows into the engine 12 through the intake manifold 120 and is monitored by the MAF sensor 124. The air is directed into the cylinder 116 and is combusted with fuel to drive pistons (not shown). Although a single cylinder 116 is illustrated, it can be appreciated that the diesel engine 104 may include additional cylinders 116. For example, diesel engines having 2, 3, 4, 5, 6, 8, 10, 12 and 16 cylinders are anticipated.

Exhaust gas resulting from the combustion within the cylinder 116 may be forced out through an exhaust manifold 132. An exhaust manifold pressure (EMP) sensor 134 located at the exhaust manifold 132 generates a signal that indicates exhaust manifold pressure.

An exhaust gas recirculation valve 136 is disposed within a conduit that communicates exhaust from the exhaust manifold 132 into the intake manifold 120. The ECM 112 may control the exhaust gas recirculation valve 136. By controlling the opening and closing of the valve 136, the amount of exhaust recirculated from the exhaust gas manifold 136 into the intake manifold 120 is known. Controlling the exhaust gas recirculation changes the amount of oxygen in the exhaust.

The exhaust treatment system 108 treats the exhaust before releasing the exhaust to the atmosphere. The exhaust treatment system 108 may include a diesel oxidation catalyst (DOC) 140, a diesel particulate filter 144, and a particulate matter (PM) sensor 148. The DOC 140 oxidizes carbon monoxide and hydrocarbons in the exhaust based on a post-combustion air/fuel ratio.

The diesel particulate filter 144 is located downstream of the DOC 140 along a flow path of the exhaust in the exhaust treatment system 108. The filter 144 removes particulate matter from the exhaust. The filter 144 may include a heater 152 located therein. The heater 152 may have various locations and configurations including extending radially across the filter 144. The heater 152 heats the exhaust and/or the filter to initiate regeneration of the filter 144. The ECM 112 controls the operation of the heater 152 as described below. In lieu of the diesel particulate filter 144, the exhaust treatment system 108 may include a diesel particulate filter that does not include a heater and is regenerated by increasing the temperature of the exhaust. For example, the exhaust temperature may be increased by the DOC 140, the engine 104, and/or other suitable mechanism.

The PM sensor 148 may be located downstream of the filter 144 along the flow path of the exhaust in the exhaust treatment system 108. The PM sensor 148 detects particulates in the exhaust flowing from the filter 144. The ECM 112 may perform multiple diagnostics, such as a protection tube diagnostic described herein, to diagnose a fault of the PM sensor 148. While the exhaust treatment system 108 is described as having only one PM sensor 148, the exhaust treatment system 108 may include more than one PM sensor 148. As an example, one PM sensor 148 may be disposed upstream of the filter 144 and another PM sensor 148 may be disposed downstream of the filter 144 for detecting the particulate matter in the exhaust before and after the filter 144.

The exhaust treatment system 108 may also include exhaust pressure sensors 156 and exhaust temperature sensors 160. The exhaust pressure sensors 156 generate signals that indicate pressures of the exhaust along the exhaust treatment system 108. The exhaust temperature sensors 160 generate signals that indicate temperatures of the exhaust at different locations along the exhaust treatment system 108. The control module 112 may generate an exhaust temperature model to estimate temperatures of the exhaust throughout the exhaust treatment system 108.

Figure 2:
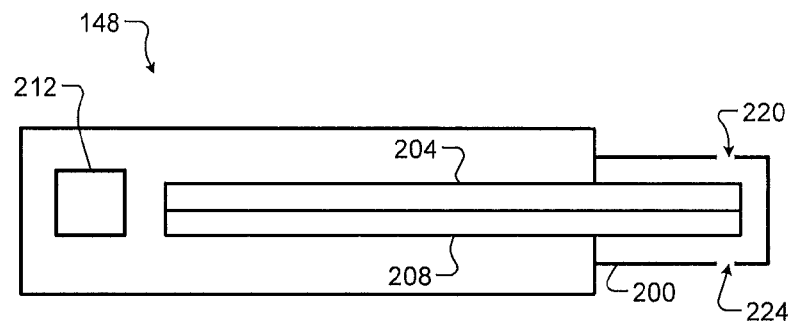
FIG. 2 illustrates an example of a particulate matter (PM) sensor of an exhaust treatment system of the engine system according to the principles of the present disclosure.

Referring to FIG. 2, an example of the PM sensor 148 is presented. The PM sensor 148 may include a protection tube 200, a detection element 204, a heating element 208, and a temperature sensor 212. The protection tube 200 may define an inlet 220 and an outlet 224. A portion of the exhaust from the filter 144 flows through the PM sensor 148 via the inlet 220 and the outlet 224.

The detection element 204 and the heating element 208 extend within the protection tube 200. The detection element 204 may sense particulate matter based on a change in electrical resistance or impedance. As an example, the detection element 204 may include a pair of electrodes disposed on a substrate with a gap disposed between the two electrodes. As exhaust flows through the PM sensor 148, particulate matter may be deposited on the electrodes of the detection element 204. The resistance between the electrodes may begin to decrease as particulate matter accumulates on the electrodes. The particulate matter may form a conductive pathway between the electrodes, through which electric current may begin to flow between the electrodes. The detection element 204 may output a signal indicative of the electric current to the ECM 112. Based on the signal from the PM sensor 148, the ECM 112 may determine the amount of particulate matter in the exhaust.

The heating element 208 heats the detection element 204 and may be integrated with the detection element 204. As an example, the heating element 208 includes a ceramic substrate. The electrodes of the detection element 204 are disposed on a surface of the ceramic substrate. The heating element 208 may be controlled by the ECM 112 to heat the PM sensor 148 to a desired temperature. The temperature sensor 212 may sense the temperature in the PM sensor 148 and output a signal indicating the temperature to the ECM 112.

Figure 3:
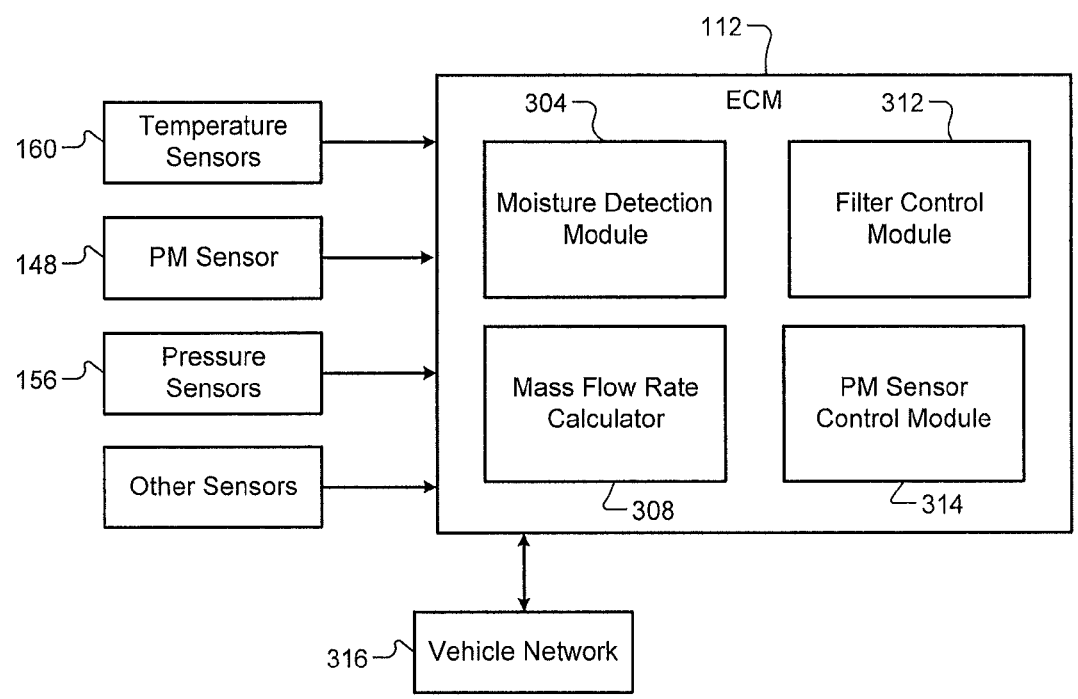
FIG. 3 is a functional block diagram of an example engine control module according to the principles of the present disclosure.

Referring to FIG. 3, an example functional block diagram of the ECM 112 is presented. The ECM 112 may include a moisture detection module 304, a mass flow rate calculator 308, a filter control module 312, and a PM sensor control module 314. The ECM 112 controls the operation of the engine 104 and components of the exhaust treatment system 108, such as the filter 144 and the PM sensor 148. The ECM 112 receives data from the pressure sensors 156, the temperature sensors 160, the PM sensor 148, and the other sensors disposed at the engine system. In addition, the ECM 112 may communicate with other modules and sensors in the vehicle via a vehicle network 316. The vehicle network 316 may be a controller area network (CAN), a local interconnect network (LIN), or other suitable communication network including wired and wireless communication.

The moisture detection module 304 determines whether the exhaust includes water vapor. Specifically, the moisture detection module 304 may estimate a dew point of water and calculate an exhaust temperature. If the exhaust temperature is below the estimated dew point, the moisture detection module 304 may determine that the exhaust flowing in the exhaust treatment system 108 includes water vapor. The exhaust temperature is generally below a dew point at engine start up. To prevent water from forming at the components, the temperature of a component such as the filter 144 and the PM sensor 148 may be increased, as described below.

The mass flow rate calculator 308 estimates a mass flow rate of exhaust traveling in the exhaust treatment system 108. As an example, the mass flow rate calculator 308 may determine the mass flow rate based on the rate of intake air from the MAF sensor 124 and a mass of fuel injected by a fuel injector in the engine 104.

The filter control module 312 controls the operation of the filter 144 and, more particularly, the heater 152. As an example, when the filter 144 is saturated with particulate matter, the filter control module 312 may clean the filter 144 by burning off the particulate matter accumulated within the filter 144. Specifically, the filter control module 312 heats the filter 144 to a combustion temperature of the particulate matter (e.g., 780° C.) via the heater 152. The filter control module 312 may also prevent water from forming or contacting the filter 144 after an engine startup by heating the filter 144 to a temperature above the estimated dew point of water (e.g., 200° C.). The filter control module 312 may control the temperature at the higher temperature until the exhaust temperature is above the estimated dew point.

The PM sensor control module 314 controls the operation of the PM sensor 148 based on data from sensors and/or information from other modules of the ECM 112. As an example, the PM sensor control module 314 may heat the PM sensor 148 to a specific range in order to clean the PM sensor 148 or prevent water from contacting the detection element 204.

Figure 4:
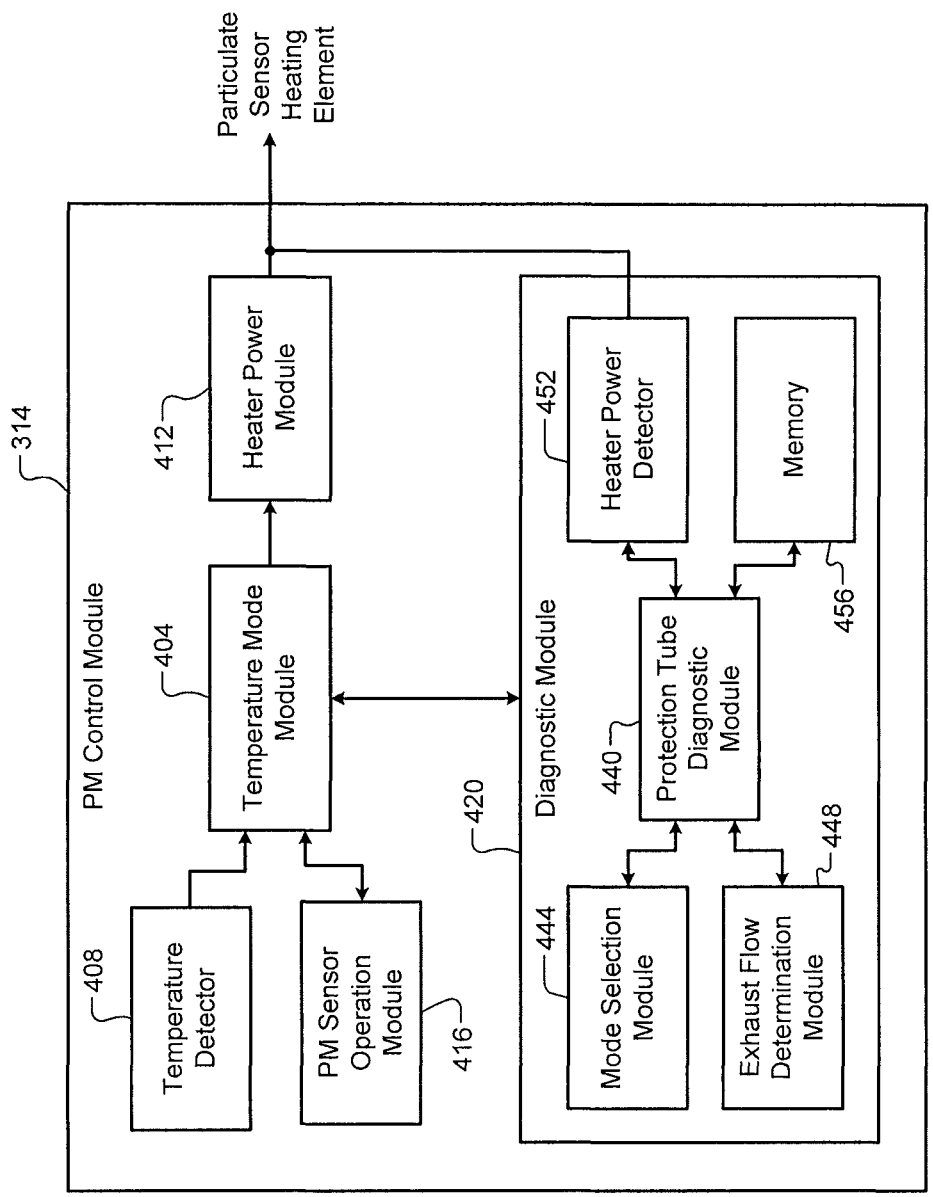
FIG. 4 is a functional block diagram of a PM sensor control module according to the principles of the present disclosure.

Referring to FIG. 4, an example functional block diagram of the PM sensor control module 314 is depicted. The PM sensor control module 314 may include a temperature mode module 404, a temperature detector 408, a heater power module 412, a PM sensor operation module 416 ("operation module 416" hereinafter), and a diagnostic module 420.

The temperature mode module 404 controls the temperature of the PM sensor 148. Specifically, the temperature mode module 404 controls the temperature of the PM sensor 148 by increasing or decreasing the temperature of the heating element 208. As an example, the temperature mode module 404 may operate the heating element 208 in one or more operation modes, such as a protective heating mode and a regeneration mode.

In the protective heating mode, the heating element 208 is controlled to heat and maintain the PM sensor 148 at or above a protective temperature set-point that is above the dew point (e.g., 200° C.). The temperature mode module 404 may maintain the protective heating mode at least until the exhaust temperature is greater than the estimated dew point.

In the regeneration mode, the heating element 208 is heated to maintain the PM sensor 148 at or above a regeneration set-point temperature that is based on the combustion temperature of the particulate matter (e.g., 780° C.). The temperature mode module 404 may maintain the regeneration mode until the particulate matter is burned off, which may be determined by the signal outputted by the PM sensor 148.

The temperature detector 408 determines a temperature of the PM sensor 148 (i.e., a PM sensor temperature). The temperature detector 408 may receive the PM sensor temperature from the temperature sensor 212 located at the PM sensor 148. The PM temperature may fluctuate due to the flow of exhaust through the PM sensor 148. More particularly, as exhaust flow through the PM sensor 148 increases, the PM sensor temperature may decrease. Accordingly, the temperature mode module 404 may increase the temperature of the heating element 208 based on the PM sensor temperature determined by the temperature detector 408.

The heater power module 412 drives the heating element 208 of the PM sensor 148 based on a signal from the temperature mode module 404. As an example, the temperature mode module 404 may determine the amount of electrical power needed to heat the heating element 208 to a desired temperature. The temperature mode module 404 may determine the power required based on the PM sensor temperature, the operation mode, the exhaust temperature, the heating properties of the heating element 208, and/or other suitable variables that may affect the heating performance of the PM sensor 148.

The operation module 416 controls the operation temperature of the PM sensor 148. More particularly, the operation module 416 may control the temperature of the PM sensor 148 to prevent water droplets from depositing on the PM sensor 148 or clean the detection element 204 to remove accumulated particulate matter from the detection element 204. To prevent water from depositing on the PM sensor 148, the operation module 416 may request the temperature mode module 404 to operate the PM sensor 148 in the protective heating mode if the temperature of the exhaust is below the estimated dew point. To clean the detection element 204, the operation module 416 may request the temperature mode module 404 to operate the PM sensor 148 in the regeneration mode if the detection element 204 is saturated with particulate matter.

The diagnostic module 420 may perform a protection tube diagnostic to determine whether exhaust is flowing through the protection tube 200 of the PM sensor 148. The protection tube diagnostic may be associated with two fault conditions, each of which may cause a failure of the protection tube diagnostic. A first fault condition may be a blockage in the protection tube 200. More particularly, if the inlet 220 and/or the outlet 224 are blocked, exhaust may not flow through the PM sensor 148. A second fault condition may be an absence of the PM sensor 148 in the exhaust treatment system 108. Specifically, the PM sensor 148 may be intentionally moved from the exhaust treatment system 108 such that the exhaust does not reach the PM sensor 148.

The diagnostic module 420 may include a protection tube diagnostic module 440, a mode selection module 444, an exhaust flow determination module 448, a heater power detector 452, and a memory 456. The protection tube diagnostic module 440 determines whether exhaust is flowing through the protection tube 200 by controlling the temperature of the PM sensor 148 at a specific operation mode and analyzing the amount of electric power needed to maintain the PM sensor 148 at a specific temperature.

The mode selection module 444 may instruct the temperature mode module 404 to control the PM sensor 148 in a desired operation mode, such as the protective heating mode or the regeneration mode. The mode selection module 444 may also instruct the temperature mode module 404 to deactivate the operation mode being performed.

The exhaust flow determination module 448 determines a flow characteristic of the exhaust flowing through the exhaust treatment system 108. The exhaust flow determination module 448 may determine the flow characteristic based on the mass flow rate provided by the mass flow rate calculator 308. The flow characteristic may include a velocity, an acceleration, and/or the calculated mass flow rate of the exhaust.

The heater power detector 452 may determine a voltage output of the heater power module 412. The heater power detector 452 may include a voltage sensor that detects the voltage being applied to the heating element 208. Accordingly, the voltage output may be the actual voltage level, an integrated voltage level that is based on the detected voltage level and a predetermined offset, and/or other suitable measurable electrical characteristic. The voltage output of the heater power module 412 may also be referred to as an electrical output.

The protection tube diagnostic module 440 may perform a diagnostic to determine whether exhaust is flowing through the protection tube 200 at engine start-up. When the protection tube diagnostic module 440 determines that no exhaust is flowing through the protection tube 200 of the PM sensor 148, the protection tube diagnostic module 440 may diagnose the PM sensor 148 with a protection tube fault and generate a diagnostic trouble code (DTC) that identifies the fault. The DTC may then be stored in the memory 456.

The diagnostic performed by the protection tube diagnostic module 440 may include a protective heating diagnostic and a regeneration diagnostic. In the protective heating diagnostic, the PM sensor 148 is operated at the protective heating mode, which may be initiated by the mode selection module 444. When the flow characteristic of the exhaust is at least at a minimum flow rate threshold, the protection tube diagnostic module 440 determines whether the voltage output of the heater power module 412 is greater than a predetermined protective power threshold. The protective power threshold may represent the minimum voltage output required for controlling the PM sensor temperature at the protective temperature set-point.

If the voltage output of the heater power module 412 is greater than the protective power threshold, the protection tube diagnostic module 440 determines that exhaust is flowing through the protection tube 200 and that the PM sensor 148 is normal. More particularly, once the PM sensor temperature is at the protective temperature set-point, the voltage output of the heater power module 412 may remain constant or slightly decrease if exhaust is not entering the PM sensor. If the PM sensor 148 is located at the correct position and the protection tube 220 is not blocked, the PM sensor temperature decreases due to the flow of exhaust through the protection tube 200. Thus, the voltage output of the heater power module 412 may increase to compensate for the drop in temperature caused by the exhaust. Conversely, if the PM sensor 148 is not located at the correct position, or the protection tube 200 is blocked, the PM sensor temperature may not decrease because there is no exhaust flowing through the protection tube 220. Thus, the voltage output of the heater power module 412 may remain the same or may decrease.

If the voltage output of the heater power module 412 is less than the protective power threshold, the protection tube diagnostic module 440 performs the regeneration diagnostic. In the regeneration diagnostic, the PM sensor 148 is operated in the regeneration mode. The regeneration mode may be initiated by the mode selection module 444.

When the flow characteristic of the exhaust is at the minimum flow rate threshold, the protection tube diagnostic module 440 determines whether the voltage output of the heater power module 412 is greater than a predetermined regeneration power threshold. The regeneration power threshold may represent the minimum voltage output needed for controlling the PM sensor temperature at the regeneration temperature set-point. The regeneration power threshold is greater than the protective power threshold.

According to the regeneration diagnostic, if the voltage output of the heater power module 412 is greater than the regeneration power threshold, the protection tube diagnostic module 440 determines that exhaust is flowing through the protection tube 200 and diagnoses the PM sensor 148 as having a normal protection tube 200. If the voltage output of the heater power module 412 is less than the regeneration power threshold, the protection tube diagnostic module 440 determines that no exhaust is flowing through the protection tube 200 and aligns the PM sensor 148 with the protection tube fault.

During the regeneration diagnostic, the PM sensor 148 is operated at a higher temperature set-point than the protective diagnostic. If exhaust is flowing through the protection tube 200, the voltage output for maintaining the PM sensor temperature is also greater during the regeneration diagnostic than the protective diagnostic. More particularly, the difference between a voltage output of a normal sensor and a faulty sensor may be greater during the regeneration diagnostic than the protective diagnostic. As an example, during the protective diagnostic, a PM sensor that is blocked may require a voltage output that is close to the protective output threshold. By performing the regeneration diagnostic, the difference between the voltage outputs of the blocked PM sensor and a normal PM sensor is much greater, such that the protection tube diagnostic module 440 may clearly distinguish between a normal sensor and faulty sensor.

In the example embodiment, the protection tube diagnostic module 440 performs the protective diagnostic and the regeneration diagnostic. Alternatively, the protection tube diagnostic module 440 may only perform the regeneration diagnostic. Specifically, after an engine start-up and once the exhaust temperature is above an estimated dew point, the protection tube diagnostic module 440 may perform the regeneration diagnostic to determine if exhaust is flowing through the PM sensor 148.

Figure 5:
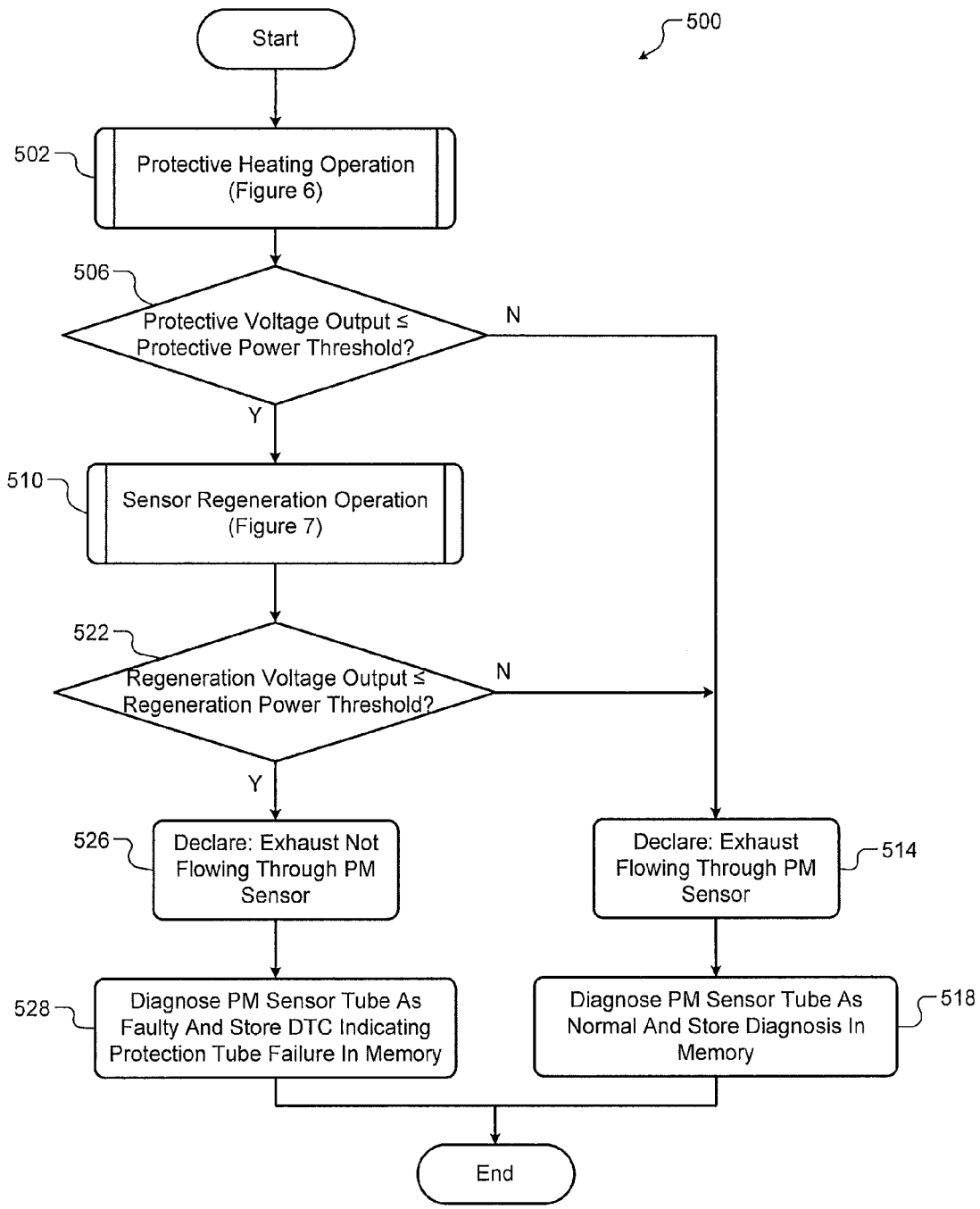
FIG. 5 illustrates an example method of diagnosing a fault of the PM sensor according to the principles of the present disclosure.

Referring to FIG. 5, a flowchart of an example diagnostic method 500 is presented. The diagnostic module 420 may perform the method 500 and may initiate the method 500 when the engine is turned on. At 502, the diagnostic module 420 performs a protective heating operation, an example of which is provided in FIG. 6. At 506, the module 420 determines whether a protective voltage output is less than a protective power threshold. Specifically, the module 420 determines whether the voltage output of the heater power module 412 during the protective heating mode is less than or equal to the predetermined protective power threshold. If the protective voltage output is less than or equal to the protective power threshold, the module 420 performs a sensor regeneration operation at 510, an example of which is provided in FIG. 7. If the protective voltage output is greater than the protective power threshold, the module 420 declares that exhaust is flowing through the protection tube 200 of the PM sensor 148 at 514. The module 420 diagnoses a normal operation of the protection tube 200 and stores information indicating the normal operation of the protection tube 200 in the memory 456 at 518.

After performing the sensor regeneration operation at 510, the module 420 determines if a regeneration voltage output is less than or equal to the regeneration power threshold at 522. If the regeneration voltage output is greater than the regeneration power threshold, the module 420 continues to 514 and 518 to diagnose a normal operation of the protection tube 200 and stores the diagnosis in the memory 456.

If the heater power output is less than or equal to the regeneration power threshold, the module 420 declares that no exhaust is flowing through the protection tube at 526 The module 420 diagnoses the PM sensor tube as faulty and stores the DTC indicating that the PM sensor tube is faulty at 528.

Figure 6:
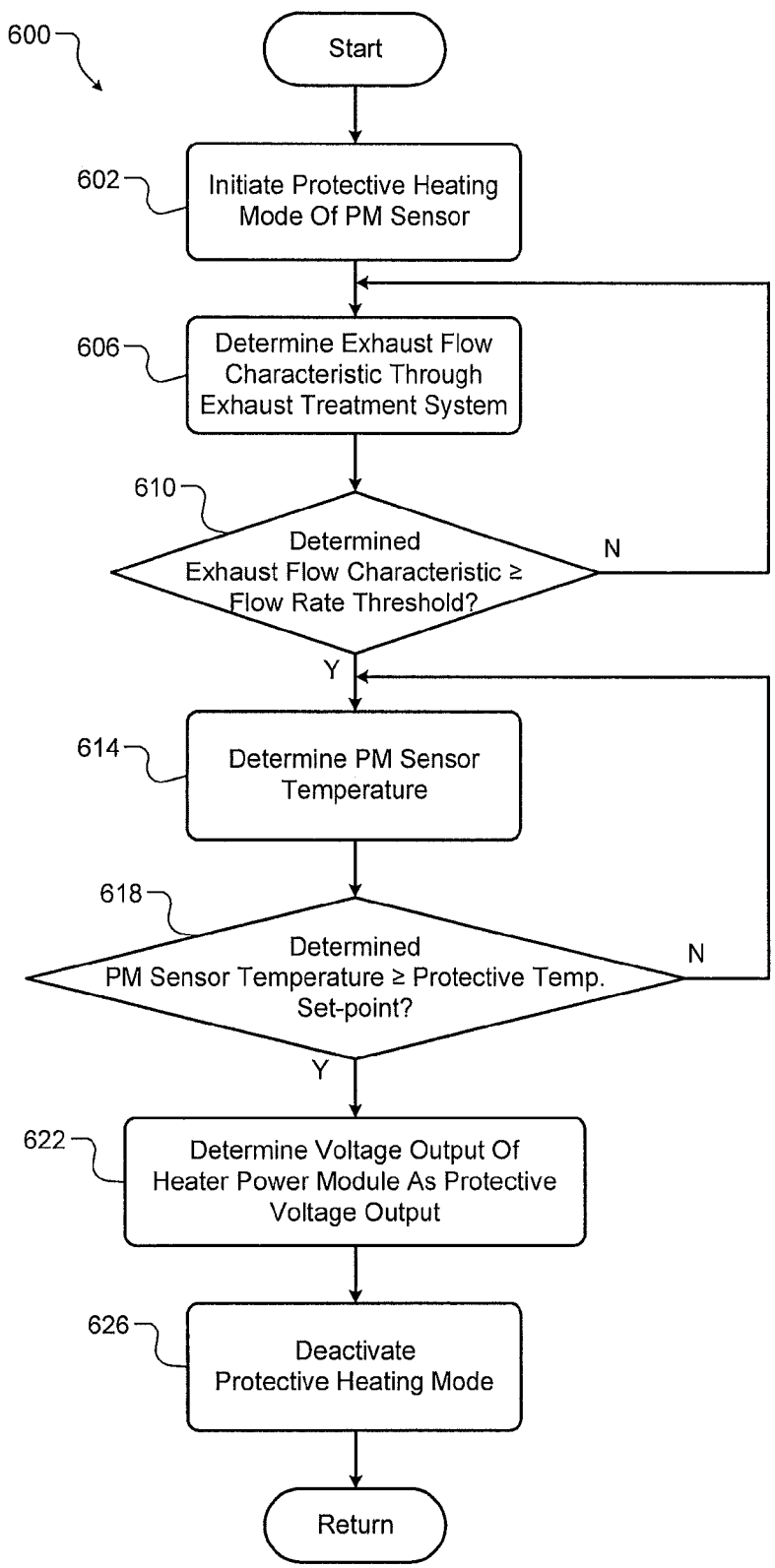
FIG. 6 illustrates an example method of performing a protective heating operation method according to the principles of the present disclosure.
Figure 7:
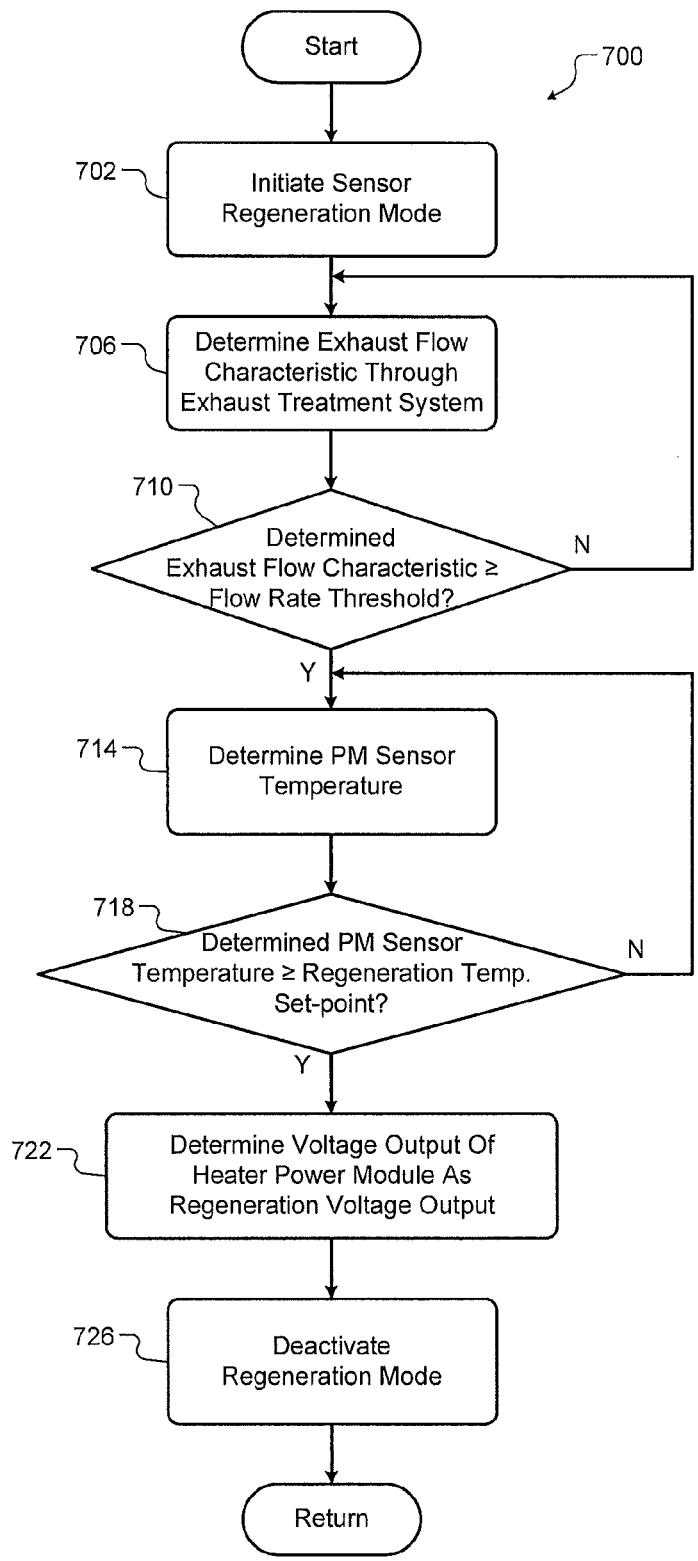
FIG. 7 illustrates an example method of performing a regeneration heating operation according to the principles of the present disclosure.

Referring to FIG. 6, a flowchart of an example protective heating operation method 600 is presented. The diagnostic module 420 may perform the method 600 and may begin the method 600 at 502 of method 500. At 602, the module 420 initiates the protective heating mode. As an example, the module 420 may request the temperature mode module 404 to operate the PM sensor 148 in the protective heating mode.

At 606 the module 420 determines the flow characteristic of the exhaust flowing through the exhaust treatment system 108 and determines whether the determined flow characteristic is greater than or equal to a flow rate threshold at 610. If the determined flow characteristic is less than the flow rate threshold, the module 420 returns to 606 until the flow characteristic reaches the flow rate threshold. If the determined flow characteristic is greater than or equal to the flow rate threshold, the module 420 determines the PM sensor temperature at 614 and determines whether the PM sensor temperature is greater than or equal to the protective temperature set-point at 618.

If the PM sensor temperature is less than the protective temperature set-point, the module 420 returns to 614 until the temperature is at least equal to the protective temperature set-point. If the PM sensor temperature is equal to or greater than the protective temperature set-point, the module 420, at 622 determines the voltage output of the heater power module 412 for maintaining the PM sensor temperature at the protective temperature set-point. The voltage output is provided as the power voltage output for the determination at 506 of method 500. At 626, the module 420 deactivates the protective heating mode of the PM sensor 148 and returns to the method 500. More particularly, the module 420 may instruct the temperature mode module 404 to deactivate the protective heating mode. In response to the deactivation, the temperature mode module may deactivate the protective heating mode once the exhaust temperature is greater than the estimated dew point Referring to FIG. 7, a flowchart of an example regeneration heating operation method 700 is presented. The diagnostic module 420 may perform the method 700 and may begin the method 700 at 510 of method 500. At 702, the module 420 initiates the regeneration mode of the PM sensor. As an example, the module 420 may request the temperature mode module 404 to operate the PM sensor 148 in the regeneration mode.

At 706 the module 420 determines the flow characteristic of the exhaust flowing through the exhaust treatment system 108 and determines whether the determined flow characteristic is greater than or equal to a flow rate threshold at 710. If the determined flow characteristic is less than the flow rate threshold, the module 420 returns to 706 until the flow characteristic reaches the flow rate threshold. If the determined flow characteristic is greater than or equal to the flow rate threshold, the module 420 determines the PM sensor temperature at 714 and determines whether the PM sensor temperature is greater than or equal to the regeneration temperature set-point at 718.

If the PM sensor temperature is less than the regeneration temperature set-point, the module 420 returns to 714 until the temperature is at least equal to the regeneration temperature set-point. If the PM sensor temperature is equal to or greater than the regeneration temperature set-point, the module 420, at 722, determines the voltage output of the heater power module 412 for maintaining the PM sensor temperature at the regeneration temperature set-point. The voltage output is provided as the regeneration voltage output for the determination at 522 of method 500. At 726, the module 420 deactivates the regeneration mode of the PM sensor 148 and returns to the method 500. More particularly, the module 420 may instruct the temperature mode module 404 to deactivate the regeneration mode. The temperature mode module 404 may deactivate the regeneration mode once the PM sensor 148 is clean.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. §112(f) unless an element is expressly recited using the phrase "means for," or in the case of a method claim using the phrases "operation for" or "step for."

What is claimed is:

1. A diagnostic module for diagnosing a particulate matter sensor in a vehicle, the diagnostic module comprising:
    a sensor mode selection module that selects a protective heating mode and a regeneration mode, wherein the regeneration mode regenerates the particulate matter sensor;
    a heater power detector that determines a protective voltage output of the particulate matter sensor in response to the selected mode being the protective heating mode and a regeneration voltage output of the particulate matter sensor in response to the selected mode being the regeneration mode; and
    a diagnostic module that performs a diagnostic of the particulate matter sensor,
    wherein the diagnostic module selectively diagnoses a fault in the particulate matter sensor in response to the protective voltage output being less than a protective power threshold and the regeneration voltage output being less than a regeneration power threshold, and selectively diagnoses the particulate matter sensor as normal in response to either the protective voltage output being greater than the protective power threshold or the regeneration voltage output being greater than the regeneration power threshold.

2. The diagnostic module of claim 1 further comprising: a flow rate determination module that determines a flow rate characteristic of exhaust flowing through an exhaust treatment system of the vehicle, wherein the diagnostic module performs the diagnostic when the flow rate characteristic is greater than or equal to a minimum flow rate threshold.

3. The diagnostic module of claim 1 wherein the heater power detector includes a voltage sensor.

4. The diagnostic module of claim 1 wherein the diagnostic module stores a diagnostic trouble code in response to diagnosing the fault in the particulate matter sensor.

5. An exhaust treatment system of a vehicle comprising:
    the diagnostic module of claim 1;
    a particulate matter sensor that detects particulate matter in exhaust and includes a heating element;
    a temperature module that controls a temperature of the particulate matter sensor to a desired temperature; and
    a heater power module that applies a voltage to the heating element based on the desired temperature.

6. The exhaust treatment system of claim 5 wherein the temperature module controls the temperature of the particulate matter sensor to a combustion temperature in the regeneration mode.

7. The exhaust treatment system of claim 5 wherein:
    the temperature module controls the temperature of the particulate matter sensor to a value greater than or equal to a dew point in the protective heating mode and controls the temperature of the particulate matter sensor to a combustion temperature in the regeneration mode.

8. A diagnostic method for diagnosing a particulate matter sensor in a vehicle, the diagnostic method comprising:
    selecting a protective heating mode and a regeneration mode for the particulate matter sensor, wherein the regeneration mode regenerates the particulate matter sensor;
    determining a voltage output as a protective voltage output during the protective heating mode and the voltage output as a regeneration voltage output during the regeneration mode; and
    selectively diagnosing a fault in the particulate matter sensor in response to the protective voltage output being less than a protective power threshold and the regeneration voltage output being less than a regeneration power threshold; and
    selectively diagnosing the particulate matter sensor as normal in response to either the protective voltage output being greater than the protective power threshold or the regeneration voltage output being greater than the regeneration power threshold.

9. The diagnostic method of claim 8 further comprising:
    determining a flow rate characteristic of exhaust flowing through an exhaust treatment system of the vehicle, wherein diagnosing the fault in the particulate matter sensor is performed when the flow rate characteristic is greater than or equal to a minimum flow rate threshold.

10. The diagnostic method of claim 8 wherein the voltage output is determined using a voltage sensor.

11. The diagnostic method of claim 8 further comprising: storing a diagnostic trouble code in response to diagnosing the fault in the particulate matter sensor.

12. The diagnostic method of claim 8 further comprising: using a heating element disposed in the particulate matter sensor, controlling a temperature of the particulate matter sensor to a desired temperature; and applying a voltage to the heating element based on the desired temperature.

13. The diagnostic method of claim 12 wherein the temperature of the particulate matter sensor is controlled to a combustion temperature in the regeneration mode.

14. The diagnostic method of claim 12 wherein:
the temperature of the particulate matter sensor is controlled to a combustion temperature in the regeneration mode, and
the temperature of the particulate matter sensor is controlled to a value greater than or equal to a dew point in the protective heating mode.

* * * * *